(12) United States Patent
Melcher et al.

(10) Patent No.: US 7,955,324 B2
(45) Date of Patent: Jun. 7, 2011

(54) CORNEA CONTACT SYSTEM

(75) Inventors: Markus Melcher, Eberbach (DE); Klaus Baumeister, Sinsheim-Adersbach (DE)

(73) Assignee: Technolas Perfect Vision GmbH, Munich (DE)

( * ) Notice: Subject to any disclaimer, the term of this patent is extended or adjusted under 35 U.S.C. 154(b) by 1372 days.

(21) Appl. No.: 11/256,649

(22) Filed: Oct. 21, 2005

(65) Prior Publication Data
US 2007/0093795 A1    Apr. 26, 2007

(51) Int. Cl.
*A61B 18/20*    (2006.01)
(52) U.S. Cl. ............... 606/10; 606/5; 128/898
(58) Field of Classification Search ........... 606/4–10; 607/88, 89; 128/898
See application file for complete search history.

(56) References Cited

U.S. PATENT DOCUMENTS

| | | | | |
|---|---|---|---|---|
| 4,905,711 A * | 3/1990 | Bennett et al. | ............ | 128/869 |
| 5,108,412 A * | 4/1992 | Krumeich et al. | ............ | 606/166 |
| 5,336,215 A * | 8/1994 | Hsueh et al. | ............ | 606/4 |
| 5,549,632 A * | 8/1996 | Lai | ............ | 606/5 |
| D459,806 S | 7/2002 | Webb | | |
| D459,807 S | 7/2002 | Webb | | |
| D462,443 S | 9/2002 | Webb | | |
| 6,730,074 B2 * | 5/2004 | Bille et al. | ............ | 606/5 |
| 6,863,667 B2 | 3/2005 | Webb et al. | | |
| 6,899,707 B2 | 5/2005 | Scholler et al. | | |
| 2002/0103481 A1* | 8/2002 | Webb et al. | ............ | 606/5 |
| 2003/0101779 A1* | 6/2003 | Chappell | ............ | 70/202 |
| 2004/0225284 A1 | 11/2004 | Webb et al. | | |
| 2005/0192562 A1* | 9/2005 | Loesel et al. | ............ | 606/5 |

FOREIGN PATENT DOCUMENTS
EP    1570822 A1    7/2005
* cited by examiner

*Primary Examiner* — Ahmed M Farah
(74) *Attorney, Agent, or Firm* — Nydegger & Associates

(57) ABSTRACT

A system for positioning the eye of a patient in alignment with a laser unit for laser surgery includes an alignment device that is mounted on the laser unit. It also includes a patient interface having a curved contact lens. Additionally, a clamp with an attached suction ring can be engaged with the interface to hold the lens against the eye of the patient. Thus, when the interface is joined with the alignment device, the lens is positioned against the eye of the patient at a predetermined distance from the laser unit for laser surgery.

16 Claims, 3 Drawing Sheets

CORNEA CONTACT SYSTEM

FIELD OF THE INVENTION

The present invention pertains generally to devices and methods that are useable for ophthalmic laser surgery. More particularly, the present invention pertains to devices and methods for aligning the eye of a patient with a laser unit for laser surgery. The present invention is particularly, but not exclusively useful as a method and device for mechanically holding the eye of a patient in alignment with a laser unit during ophthalmic laser surgery.

BACKGROUND OF THE INVENTION

During ophthalmic laser surgery, it is of paramount importance that the eye of a patient be held, and maintained, in a proper optical alignment with the laser unit that is to be used for the surgery. When this alignment is to be accomplished mechanically, it is necessary to move the patient into alignment with the laser unit, or move the laser unit into alignment with the patient. Either way, some mechanism that directly engages the eye with the laser unit must be established.

Depending on such factors as the nature of the surgery, the condition of the patient, and the operational capabilities of the laser unit, it may be preferable to pre-position a contact lens against the eye of the patient. And, do so before establishing the requisite optical alignment between the eye and the laser unit. On the other hand, in another situation, these same factors may dictate that it is preferable to first engage the contact lens with the laser unit. And, then establish a proper optical alignment between the eye and the laser unit. Regardless of the preferred sequence of actions, in the end it is important that the contact lens be placed against the anterior surface of the eye, and that the contact lens be positioned at a predetermined distance from the laser unit.

In light of the above, it is an object of the present invention to provide systems and methods for positioning the eye of a patient in alignment with a laser unit that fixes the eye at a predetermined distance from the laser unit. Another object of the present invention is to provide systems and methods for positioning the eye of a patient in alignment with a laser unit that allows the flexibility of either moving the patient into contact with the laser unit, or moving the laser unit into contact with the patient. Still another object of the present invention is to provide systems and methods for positioning the eye of a patient in alignment with a laser unit that are easy to use or implement, that are simple to manufacture or operate, and that are comparatively cost effective.

SUMMARY OF THE INVENTION

A system for positioning the eye of a patient for laser surgery includes a patient interface that brings a curved contact lens into contact with the eye. During this contact, the lens is held stationary on the anterior surface of the eye. Also, the interface is joined with a laser unit to establish an optical alignment that positions the lens with a predetermined distance between the patient's eye and the laser unit. In accordance with the present invention, contact between the interface and the eye for laser surgery can be accomplished either before, or after, the interface is joined with the laser unit.

In overview, the major components of the eye positioning system of the present invention are: a suction ring that is attached to a clamp; the patient interface that carries with it a curved contact lens; and an alignment device that is mounted on the laser unit. In detail, the suction ring and the clamp are integrally connected in a unitary construction. In this combination, the clamp is presented as a scissors-like mechanism that can be manipulated to close onto the patient interface. The clamp can then be locked to hold the patient interface on the suction ring. In detail, the clamp defines an orifice, and the clamp is moveable between a first configuration wherein the clamp can receive the patient interface in the orifice, and a second configuration wherein the clamp closes the orifice onto the patient interface. In its second configuration the clamp fixedly holds the patient interface on the clamp.

Structurally, the clamp has a first handle, with the suction ring rigidly affixed thereto. The clamp also has a second handle that is mounted on the first handle for rotation about a pivot point. This rotation alternatively establishes either the first configuration or the second configuration for said clamp. In order to establish limits for this rotation, the first handle is formed with a pin, and the second handle is formed with a slot for receiving the pin. In this combination, the handles interact with each other to restrict their relative movement between the first and second configurations. Additionally, the first handle is formed with a first latch and the second handle is formed with a second latch that engage with each other to hold and selectively maintain the clamp in its second configuration.

As for the patient interface, it is formed with a receptacle and, as indicated above, it includes the curved contact lens. The alignment device, which is mounted directly onto the laser unit, is dimensioned to be received into the receptacle of the patient interface. Importantly, as indicated above, this cooperation of structure positions the curved contact lens at a predetermined distance from the laser unit.

For the operation of the system, the suction ring is positioned to surround a target area on the eye's anterior surface where the laser surgery is to be performed. A suction device is then activated to hold the suction ring in place on the eye. Next, the curved contact lens of the patient interface is positioned within the suction ring such that the curved contact lens is placed in contact with the target area on the anterior surface of the eye. Once the curved contact lens is in place, the clamp is activated to fixedly hold the patient interface within the suction ring. Also, when the clamp is activated, the curved contact lens is held stationary against the target area on the anterior surface of the eye.

Optical alignment of the patient's eye with the laser unit for conducting laser surgery is essentially established in a two-step operation. In one step, the patient interface is engaged with the alignment device on the laser unit. In the other step, the patient interface is engaged with the suction ring, as it surrounds the target area on the eye. As implied above, either step can be accomplished first. Regardless of the particular attachment sequence, the interconnection of components is always similarly accomplished. Specifically, the patient interface and the alignment device are held together by a suction mechanism. On the other hand, the patient interface is held on the suction ring by the clamp.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
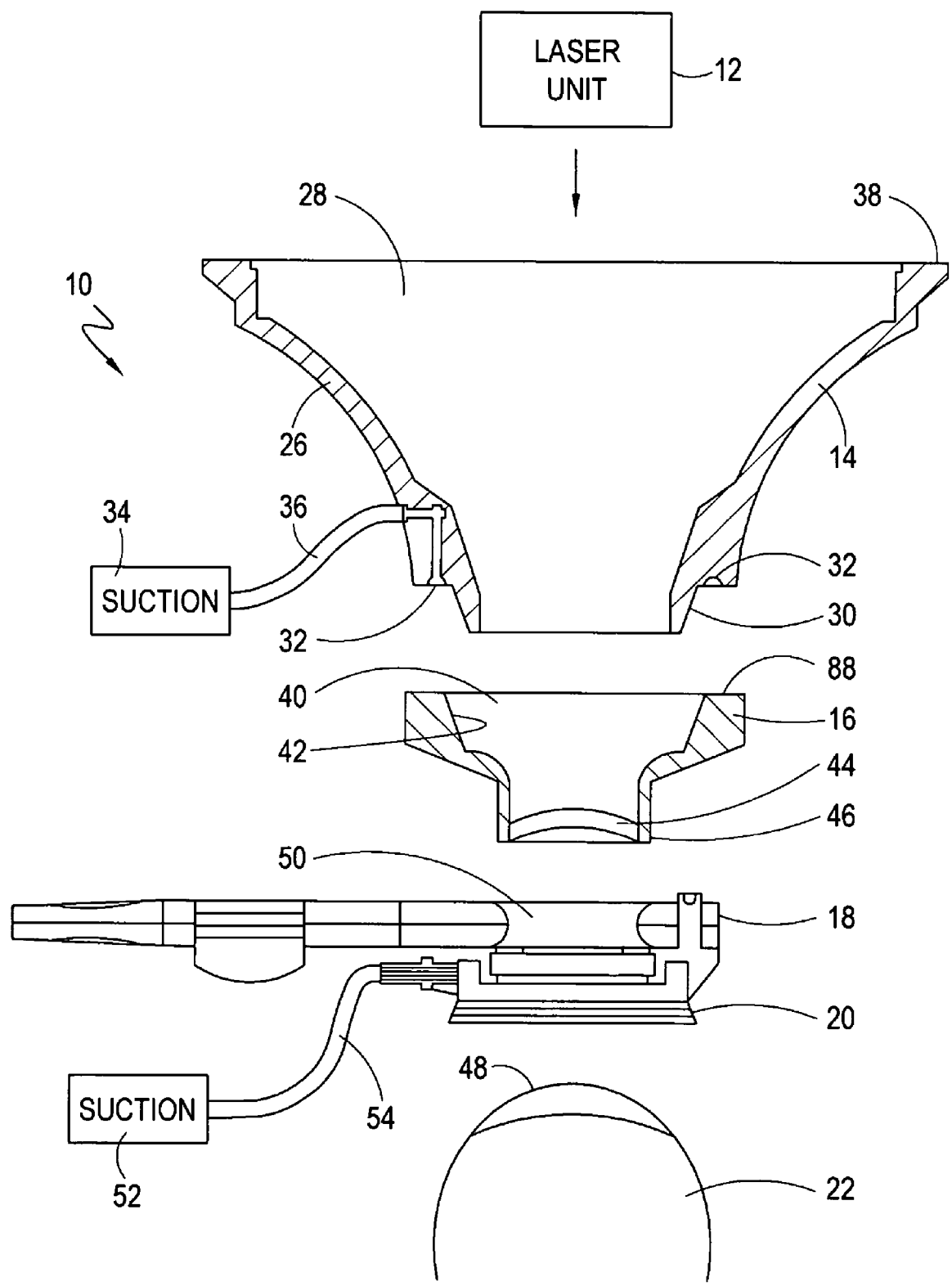
FIG. 1 is an exploded view of the system of the present invention in combination with an eye of a patient, and with portions shown in cross-section for clarity.
Figure 2:
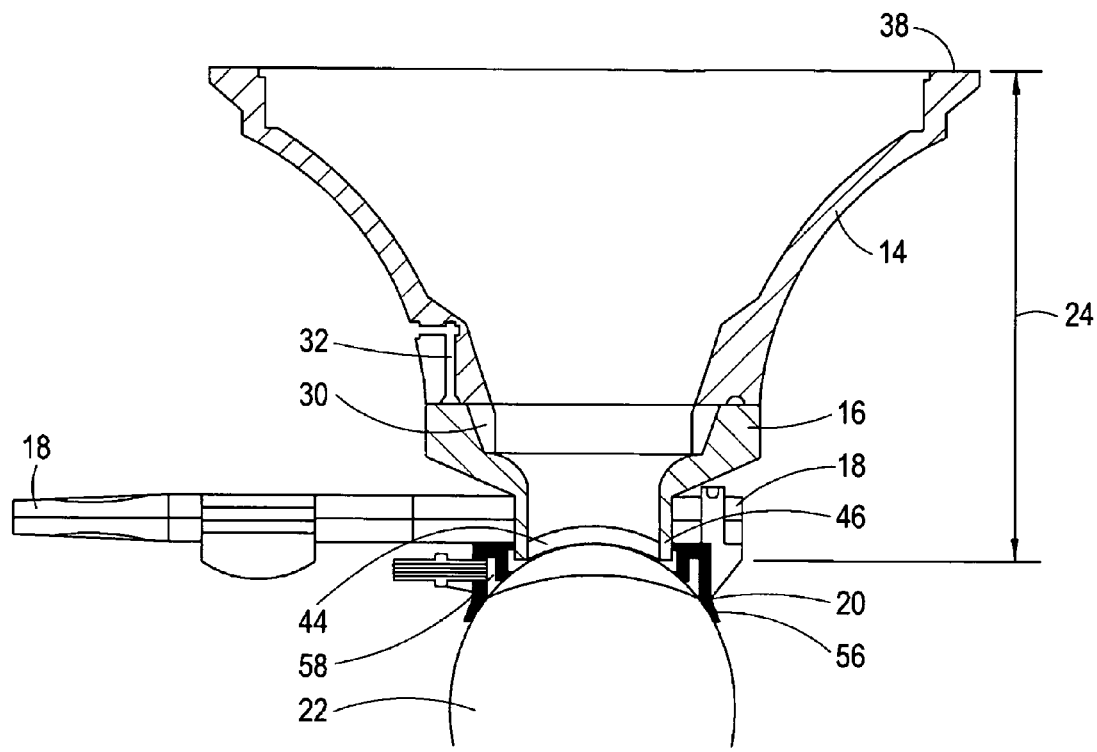
FIG. 2 is a connected view of the system shown in FIG. 1.

Referring initially to FIG. 1, the components of a system in accordance with the present invention are shown and collectively designated 10. As shown, the system 10 essentially includes a laser unit 12 and an alignment device 14 that is fixedly mounted on the laser unit 12. Further, the system 10 includes a patient interface 16 and a clamp 18. As envisioned for the present invention, a suction ring 20 is integrally attached to the clamp 18. In overview, during a surgical procedure, the suction ring 20 is positioned on the eye 22 of a patient, and the interface 16 is engaged between the alignment device 14 and the clamp 18 as generally shown in FIG. 2. The object of this structural combination is to position and maintain the eye 22 of a patient at a predetermined distance 24 (see FIG. 2) from the laser unit 12 during the surgical procedure.

FIG. 1 shows that the alignment device 14 includes a wall 26 that surrounds an open passageway 28. Further, the wall 26 is formed with a tapered insert 30, and it has a suction channel 32 that is connected in fluid communication with a suction device 34 via a hose 36. As stated above, and indicated in FIG. 1, the end 38 of alignment device 14 is fixedly mounted on the laser unit 12. This can be accomplished in any manner well known in the pertinent art.

Still referring to FIG. 1 it will be seen that the patient interface 16 is formed with an open passageway 40 and includes a tapered receptacle 42. As required for the system 10 of the present invention, the taper of receptacle 42 in the patient interface 16 is compatible with the taper of the insert 30 on the alignment device 14. This compatibility allows for a mating engagement of the alignment device 14 with the patient interface 16, as shown in FIG. 2. In FIG. 1 it is also seen that a curved contact lens 44 is mounted at the end 46 of the patient interface 16 and, thus, is presented as an integral part of the patient interface 16. With this in mind, it is to be appreciated that the curved contact lens 44 and the patient interface 16 can be manufactured as a one-piece unit. The consequence of all this is that when the alignment device 14 is joined with the patient interface 16, the end 46 of the patient interface 16 (i.e. lens 44) will be at a predetermined distance 24 from the end 38 of alignment device 14 (i.e. laser unit 12). Further, the curved contact lens 44 is manufactured with a radius of curvature that generally conforms with the anterior surface 48 of the eye 22.

Figure 3:
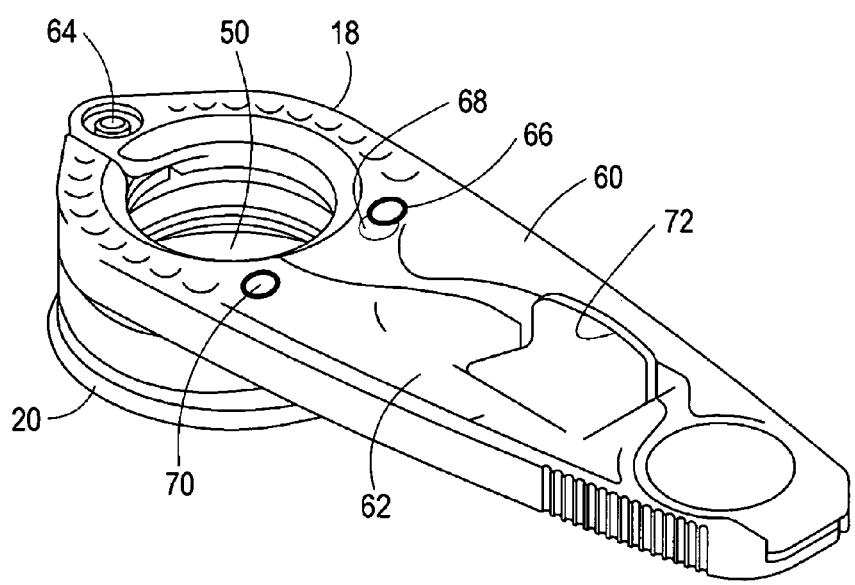
FIG. 3 is a perspective view of the clamp used in the system of the present invention.

Referring now to FIG. 3 it will be seen that the clamp 18 is formed with an orifice 50. In FIG. 3 it will also be seen that the suction ring 20 substantially surrounds the orifice 50. Returning for the moment to FIG. 1, it will be seen there that the suction ring 20 is connected in fluid communication with a suction device 52, via a hose 54. In more detail, FIG. 2 shows that the suction ring 20 includes a pliable skirt 56 that forms a suction passageway 58 for the suction ring 20. Consequently, when the clamp 18 is engaged with the patient interface 16, the suction ring 20 can be used to hold the contact lens 44 against the anterior surface 48 of the eye 22.

Figure 4:
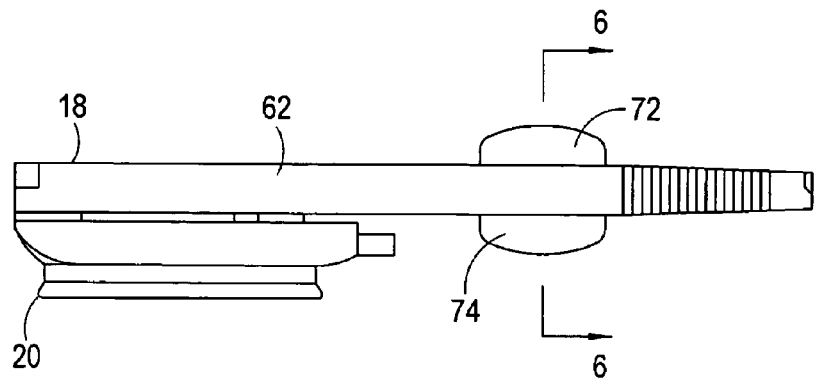
FIG. 4 is a side view of the clamp, in combination with a suction ring of the present invention.

FIG. 3 also shows that the clamp 18 includes a handle 60 and a handle 62. In detail, the handle 62 is joined to the handle 60 at a pivot point 64 for relative rotation between the handles 60 and 62. Structurally, the pivot point 64 is a pin that extends from the suction ring 20. Further, the suction ring 20 is formed with a pin 66 that extends therefrom and is received in a slot 68 that is formed on the handle 60. Thus, a rotation of the handle 60 on the handle 62, about the pivot point 64, is limited by the interaction of the pin 66 in slot 68. Also, as may be best appreciated by referencing FIG. 3 with FIG. 4, the suction ring 20 is held against the handle 62 by a pin 70, as well as by any adhesive or bonding that may be used. Further, as best appreciated with reference to both FIG. 3 and FIG. 4, the clamp 18 includes a latch 72 and a latch 74 that are, respectively, attached to the handle 62 and the handle 60. As envisioned for the present invention, the handles 60 and 62 are essentially identical in structure. In combination, they are joined together with one handle (e.g. handle 62) oriented upside down relative to the other handle (e.g. handle 60).

Figure 5A:
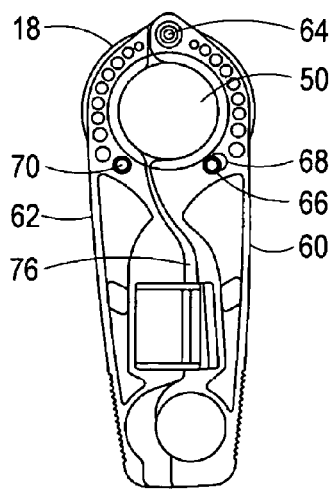
FIG. 5A is a top view of the clamp in its first configuration.
Figure 5B:
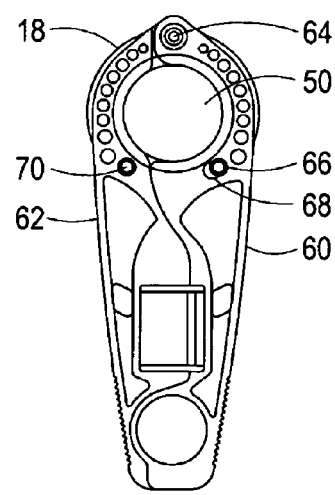
FIG. 5B is a top view of the clamp in its second configuration.

The interaction of handles 60 and 62 of the clamp 18 will be best appreciated with reference to FIGS. 5A and 5B. For purposes of the present invention, as shown, the clamp 18 is moveable between a first (open) configuration (FIG. 5A) and a second (closed) configuration (FIG. 5B). Specifically, in the first configuration, the handle 60 is rotated, and thereby distanced from the handle 62 by a separation 76. An important consequence of this first configuration is that the orifice 50 is sufficiently enlarged to receive the end 46 of patient interface 16, and curved contact lens 44, into the orifice 50. The clamp 18 can then be moved into its second configuration. The consequence of this second configuration is that the orifice 50 is constricted to engage the clamp 18 as the handles 60 and 62 are closed on each other to eliminate the separation 76. Specifically, with the clamp 18 in its second configuration (FIG. 5B), the end 46 of the patient interface 16 is fixedly held on the clamp 18.

Figure 6A:
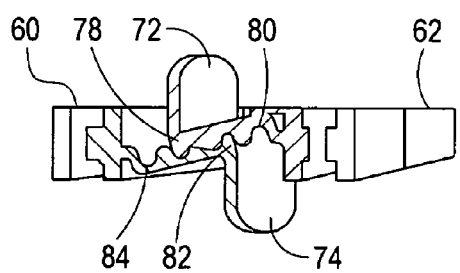
FIG. 6A is a cross-section view of the clamp as seen along the line 6-6 in FIG. 4 when the clamp is in its first (open) configuration.
Figure 6B:
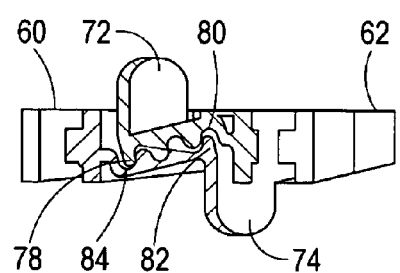
FIG. 6B is a cross-section view of the clamp shown in FIG. 6A when the clamp is in its second (closed) configuration.

FIGS. 6A and 6B respectively pertain to the first configuration (FIG. 5A) and the second configuration (FIG. 5B) of the clamp 18. More specifically, by comparing FIG. 6A with FIG. 6B, the interaction of the latches 72 and 74 can be appreciated. As shown, the latch 72 is formed with a projection 78 and a detent 80. Similarly, the latch 74 is formed with a projection 82 and a detent 84. When the clamp 18 is in the first configuration (FIG. 6A), the latches 72 and 74 do not engage each other. In the second configuration (FIG. 6B), however, it can be seen that the projection 78 of latch 72 is engaged with the detent 84 of the latch 74. At the same time, the projection 82 of the latch 74 engages with the detent 80 of latch 72. Thus, the clamp 18 can be maintained in the second configuration (FIGS. 5B and 6B) until an operator disengages the latches 72,74 for a return of the clamp 18 to its first (open) configuration (FIGS. 5A and 6A).

In the operation of the system 10 of the present invention, it is to be first understood that the alignment device 14 is fixedly mounted onto the laser unit 12. Thus, the end 38 of the alignment device 14 has a fixed spatial relationship with the optics (not shown) of the laser unit 12. With this in mind, the suction ring 20 of clamp 18 is located, as desired, on the anterior surface 48 of the eye 22. Specifically, the suction ring 20 is located to surround a target area on the anterior surface 48 where the laser surgery is to be conducted. At this point in the operation, the clamp 18 is in its first configuration (see FIGS. 5A and 6A). The suction device 52 is then activated to create a partial vacuum in the suction passageway 58 of suction ring 20. This action holds the clamp 18 on the eye 22.

With the clamp 18 and suction ring 20 positioned on the eye 22, the end 46 of patient interface 16 can then be inserted into the orifice 50 of the clamp 18. As this is done, the curved contact lens 44 is positioned against the anterior surface 48 of the eye 22 to substantially conform the lens 44 with the surface 48. Clamp 18 is then closed. Specifically, as the clamp 18 is closed, the configuration of the clamp 18 is manually changed from it first (open) configuration (FIGS. 5A and 6A) to its second (closed) configuration (FIGS. 5B and 6B). Thus, the patient interface 16 is held by the clamp 18, with the curved contact lens 44 against the eye 22 of the patient.

An engagement of the patient interface 16 with the alignment device 14 is accomplished by receiving the tapered insert 30 of the alignment device 14 into the tapered receptacle 42 of the patient interface 16. This engagement also positions the suction channel 32 of the alignment device 14 against the abutment 88 of the patient interface 16. Consequently, with the activation of the suction device 34, a partial vacuum in the suction channel 32 will fixedly hold the alignment device 14 against the patient interface 16. Importantly, this fixed engagement also locates the curved contact lens 44 at the predetermined distance 24 from the end 38 of the alignment device 14. Thus, it also holds the curved contact lens 44 at the predetermined distance 24 from the optics of the laser unit 12. The consequence of all this is a combination of the components of the system 10 as generally shown in FIG. 2. The desired laser surgery can then be performed.

In an alternative to the set-up described above, it is also possible to join the patient interface 16 with the alignment device 14 before it is engaged with the clamp 18. Subsequently, the patient interface 16 can be joined with the clamp 18, as described above. This choice provides the flexibility of first joining the patient interface 16 with either the alignment device 14 or the clamp 18. And, subsequently joining the patient interface 16 with the other as-yet-unconnected component. As indicated above, the exact sequence of the task for combining the components of the system 10 is a matter of choice and will depend on the particular requirements of the surgical procedure, and of the laser unit 12.

While the particular Cornea Contact System as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A system for positioning the eye of a patient for laser surgery which comprises:
   a laser unit for generating a laser beam;
   an alignment device mounted on said laser unit;
   a patient interface having a first end formed with a receptacle for receiving said alignment device therein and a second end for holding a contact lens thereon;
   a two-piece scissor-type clamp defining an orifice, the clamp having a first handle with a first latch and a second handle with a second latch, said clamp being moveable between a first configuration wherein the first handle is spread from the second handle to receive the second end of said patient interface in the orifice, and a second configuration wherein the first handle is juxtaposed with the second handle to close the orifice onto the patient interface and to fixedly hold the second end of said patient interface on said clamp, wherein said clamp is selectively locked in its second configuration by the engagement of the first latch with the second latch; and
   a suction ring attached to said clamp to surround the orifice and hold the contact lens at the second end of the patient interface against the eye of the patient when said interface is held by said clamp, and said alignment device is received in the receptacle of the first end of the patient interface for laser surgery.

2. A system as recited in claim 1 wherein the curved contact lens is mounted on the second end of said patient interface for positioning of said lens against the eye of the patient at a predetermined distance from said laser unit during laser surgery.

3. A system as recited in claim 1 further comprising a suction means connected to said suction ring to create a suction therewith for holding said suction ring in position against the eye to surround a target area thereon where the laser surgery is to be performed.

4. A system as recited in claim 1 wherein said alignment device is formed with a suction channel and said system further comprises a suction means connected in fluid communication with said suction channel to create a suction for holding said patient interface against said alignment device.

5. A system as recited in claim 1 wherein said suction ring is rigidly affixed to said first handle and said second handle is mounted on said first handle for rotation about a pivot point thereon to establish the first configuration and, alternatively, to establish the second configuration for said clamp.

6. A system as recited in claim 5 wherein said first handle is formed with a pin, and said second handle is formed with a slot for receiving said pin therein to interact therewith to restrict relative movement of said first and second handles between the first and second configurations.

7. A system for positioning the eye of a patient in alignment with a laser unit for laser surgery which comprises:
   an alignment device;
   a patient interface having a first end formed with a receptacle for receiving said alignment device therein and a second end for holding a contact lens thereon;
   a two-piece scissor-type clamp defining an orifice, the clamp having a first handle with a first latch and a second handle with a second latch, said clamp being moveable from a first configuration wherein the first handle is spread from the second handle to receive the second end of said patient interface in the orifice, and a second configuration wherein the first handle is juxtaposed with the second handle to close the orifice onto the second end of the patient interface to fixedly hold said patient interface on said clamp, wherein said clamp is selectively locked in its second configuration by the engagement of the first latch with the second latch and wherein the alignment device is mounted on the laser unit for engagement with the first end of said patient interface to align the eye of the patient with the laser unit for laser surgery; and
   a suction ring attached to said clamp to surround the orifice and hold the patient interface against the eye of the patient when said interface is held by said clamp.

8. A system as recited in claim 7 wherein the contact lens is curved and is mounted on said patient interface for positioning of said lens against the eye of the patient at a predetermined distance from said laser unit during laser surgery.

9. A system as recited in claim 7 further comprising:
   a first suction means connected to said suction ring to create a suction for holding said suction ring in position against the eye to surround a target area thereon where the laser surgery is to be performed; and a second suction means for creating a suction to hold said patient interface against said alignment device.

10. A system as recited in claim 7 wherein said clamp further comprises a locking mechanism for selectively maintaining the second configuration of said clamp.

11. A system as recited in claim 7 wherein said suction ring is rigidly affixed to said first handle and said second handle is mounted on said first handle for rotation about a pivot point thereon to establish the first configuration and, alternatively, to establish the second configuration for said clamp.

12. A system as recited in claim 11 wherein said first handle is formed with a pin, and said second handle is formed with a slot for receiving said pin therein to interact therewith to restrict relative movement of said first and second handles between the first and second configurations.

13. A method for positioning the eye of a patient in alignment with a laser unit for laser surgery which comprises the steps of:

mounting an alignment device on the laser unit;

locating a suction ring on the eye of the patient to surround a target area thereon where the laser surgery is to be performed, wherein the suction ring is attached to a two-piece scissor-type clamp defining an orifice, the clamp having a first handle with a first latch and a second handle with a second latch and said clamp is moveable between a first configuration wherein the first handle is spread from the second handle and a second configuration wherein the first handle is juxtaposed with the second handle, and wherein said clamp is selectively locked in its second configuration by the engagement of the first latch with the second latch;

holding a patient interface with said clamp, wherein said patient interface has a first end formed with a receptacle and a second end with a contact lens mounted thereon, and wherein said holding step is accomplished by moving the clamp from its first configuration wherein said clamp receives the second end of said patient interface in the orifice, and its second configuration wherein said clamp closes the orifice onto the second end of the patient interface to fixedly hold said patient interface on said clamp; and receiving the alignment device into the receptacle at the first end of said patient interface to align said patient interface with the laser unit for laser surgery.

14. A method as recited in claim 13 wherein said holding step is accomplished before said receiving step.

15. A method as recited in claim 13 wherein said receiving step is accomplished before said holding step.

16. A method as recited in claim 13 wherein said clamp comprises said suction ring rigidly affixed to the first handle, and the second handle mounted on said first handle for rotation about a pivot point thereon to establish the first configuration and, alternatively, to establish the second configuration for said clamp, and wherein said first handle is formed with a pin, and said second handle is formed with a slot for receiving said pin therein to interact therewith to restrict relative movement of said first and second handles between the first and second configurations.

* * * * *